US006973345B2

(12) United States Patent
Yamazaki et al.

(10) Patent No.: US 6,973,345 B2
(45) Date of Patent: *Dec. 6, 2005

(54) EXERCISE LOAD MEASURING INSTRUMENT WITH BODY FAT MEASURING FUNCTION

(75) Inventors: Iwao Yamazaki, Tokyo (JP); Kimiyo Yamazaki, Tokyo (JP)

(73) Assignee: YA-MAN Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 533 days.

(21) Appl. No.: 10/181,414

(22) PCT Filed: Jan. 25, 2001

(86) PCT No.: PCT/JP01/00487

§ 371 (c)(1),
(2), (4) Date: Jul. 23, 2002

(87) PCT Pub. No.: WO01/54582

PCT Pub. Date: Aug. 2, 2001

(65) Prior Publication Data

US 2002/0193702 A1 Dec. 19, 2002

(30) Foreign Application Priority Data

Jan. 25, 2000 (JP) .............................. 2000-016229

(51) Int. Cl.[7] .............................................. A61F 5/05
(52) U.S. Cl. ..................................... 600/547; 128/921
(58) Field of Search ............................... 600/547, 595, 600/300; 128/920, 921

(56) References Cited

U.S. PATENT DOCUMENTS

| 6,506,152 B1 * | 1/2003 | Lackey et al. .............. 600/300 |
| 6,694,182 B1 * | 2/2004 | Yamazaki et al. .......... 600/547 |

FOREIGN PATENT DOCUMENTS

| JP | 06078827 A | * | 3/1994 |
| JP | 08126632 | * | 5/1996 |
| JP | 11042220 A | * | 2/1999 |
| JP | 11126015 A | * | 5/1999 |
| JP | 11332845 A | * | 12/1999 |

* cited by examiner

Primary Examiner—Eric F. Winakur
(74) Attorney, Agent, or Firm—Bacon & Thomas

(57) ABSTRACT

Disclosed is an exercise amount measuring device comprising: means for calculating the body fat percentage from the bioelectrical impedance of an individual and the personal data of the individual; means for determining the body shape of the individual and the amount of the basal metabolism of the individual from the personal data and the calculated body fat percentage; means for calculating the "to-be-consumed" body fat amount by subtracting a given body fat percentage set for a goal from the measured body fat percentage; means for calculating the "to-be-consumed" calorie amount required for reducing the "to-be-consumed" body fat amount; means for changing the "to-be-consumed" calorie amount to the corresponding amount of exercise and for setting the so converted amount of exercise as a goal; means for calculating the actual amount of exercise and the consumed calorie amount from the detected motions of the living body and the acceleration of the motion of the living body; and means for calculating the remaining "to-be-consumed" calorie amount, which is given by subtracting the consumed calorie amount from the "to-be-consumed" calorie amount, and the remaining "to-be-attained" exercise amount.

12 Claims, 6 Drawing Sheets

BODY FAT PERCENTAGE (%)

① Below a Normal Health Range

② A Normal Health Range

③ Above a Normal Health Range

EXERCISE LOAD MEASURING INSTRUMENT WITH BODY FAT MEASURING FUNCTION

TECHNICAL FIELD

The present invention relates to an exercise amount measuring device provided with a body fat measuring function, which device is responsive to the two- or three-dimensional movement of one's body for determining the amount of exercise.

BACKGROUND ART

The total calorie amount consumed per day within one's body can be determined by summarizing the calorie amount consumed by motions in daily life and exercises and the amount of the basal metabolism consumed irrespective of physical exercise.

The calorie amount consumed by taking an exercise depend on the length of time for which a person takes the exercise and the kind of exercise which the person takes (mode of movement), and on the amount of the basal metabolism of the person. Assuming that an athletic person whose basal metabolism amount is large and an overweight or fat person whose basal metabolism amount is small take one and same exercise, the calorie amount consumed by the athletic person is larger than that consumed by the overweight person; energy is liable to be consumed much more in muscles than in fat, and accordingly the calorie amount consumed in muscles is larger than in fat. Therefore, muscular people whose basal metabolism amount is large can consume much more calorie than overweight people whose basal metabolism amount is small when taking one and same exercise.

As may be apparent from the above, the calorie amount consumed by exercise should be rightly calculated by taking the amount of the individual basal metabolism into account, and the amount of the individual basal metabolism can be determined in terms of the fat-free weight, which apparently represents the amount of muscles, and can be determined by subtracting the body fat from the weight.

The fat-free weight cannot be determined without measuring the body fat percentage.

A conventional exercise amount measuring device has no function of measuring the body fat percentage, and therefore, it cannot distinguish an athletic person from an overweight person. Consequently the conventional exercise amount measuring device calculates incorrectly the calorie amount consumed by an exercise irrespective of which type of person takes the weight, an athletic person or an overweight person. In other words the consumed calorie amount is calculated irrespective of the amount of the individual basal metabolism.

Also, it should be noted that: the conventional exercise amount measuring device shows the amount of exercise and/or the calorie amount actually consumed by an exercise, but the device does not permit a user to: preset an amount of exercise as a goal, at which the user will be satisfied with the effect on the losing of his or her weight; make a decision as to whether or not the present amount of exercise is appropriate for the purpose; and realize the effect caused by the exercise taken by the person.

For these reasons people using such exercise amount measuring devices are apt to be bored sooner or later, not using them effectively for a long time. The amount of calories consumed is dependent on each mode of movement, but the conventional exercise amount measuring device cannot make any distinction between different modes of movement, and therefore, it cannot calculate with good accuracy.

In view of the above one object of the present invention is to provide an exercise amount measuring device provided with a body fat measuring function and a capability of determining which mode of movement, thereby permitting the calorie amount consumed by an exercise to be determined by taking the amount of the individual basal metabolism and the mode of movement into account so that the accuracy in calculation may be significantly improved, and at the same time, permitting a person using the device to preset an amount of exercise as a goal and permitting the person to realize the effect caused by the exercise on the way to the goal.

DISCLOSURE OF THE INVENTION

To attain this object an exercise amount measuring device provided with a body fat measuring function according to claim 1 comprises:
 a wearable casing having a display mounted on its front;
 electrodes appearing on the surface of the casing for measuring the bioelectrical impedance of a person who is using the device;
 personal data inputting means for inputting the sex, age, height and weight of the person;
 body fat percentage calculating means for determining the body fat percentage of the person from the personal data and the bioelectrical impedance of the person;
 basal metabolism calculating means for calculating the amount of the basal metabolism of the person from the personal data and the body fat percentage of the person;
 means for presetting a given body fat percentage as a goal;
 "to-be-reduced" body fat amount calculating means for determining the amount of "to-be-reduced" body fat from the difference between the present body fat percentage and the given body fat percentage preset as the goal;
 "to-be-reduced" calorie amount calculating means for calculating the calorie amount to be reduced for consuming the amount of "to-be-reduced" body fat;
 exercise amount measuring means responsive to two- or thee-dimensional movement for measuring the amount of exercise and for determining which mode of movement; and
 consumed calorie amount measuring means for determining the calorie amount consumed actually by the exercise from the so measured amount of exercise, the so determined mode of movement and the so calculated amount of the basal metabolism of the person; whereby the "to-be-reduced" calorie amount and the calorie amount actually consumed by the exercise taken by the person in addition to the body fat percentage may be given in the display An exercise amount measuring device provided with a body fat measuring function according to claim 2 comprises:
 a wearable casing having a display mounted on its front;
 electrodes appearing on the surface of the casing for measuring the bioelectrical impedance of a person who is using the device;
 personal data inputting means for inputting the sex, age, height and weight of the person;
 body fat percentage calculating means for determining the body fat percentage of the person from the personal data and the bioelectrical impedance of the person;
 basal metabolism calculating means for calculating the amount of the basal metabolism of the person from the personal data and the body fat percentage of the person;

means for presetting a given body fat percentage as a goal;

"to-be-reduced" body fat amount calculating means for determining the amount of "to-be-reduced" body fat from the difference between the present body fat percentage and the given body fat percentage preset as the goal;

"to-be-reduced" calorie amount calculating means for calculating the calorie amount to be reduced for consuming the amount of "to-be-reduced" body fat;

exercise amount measuring means responsive to two- or thee-dimensional movement for measuring the amount of exercise the so determined mode of movement;

consumed calorie quantity measuring means for determining the caloric quantity consumed actually by the physical exercise from the so measured amount of exercise the so determined mode of movement and the so calculated basal metabolism; and remaining calorie amount calculating means for calculating the remaining calorie amount to be reduced by subtracting the actually consumed calorie amount from the "to-be-reduced" calorie amount;

whereby the remaining calorie amount in addition to the body fat percentage may be given in the display.

An exercise amount measuring device provided with a body fat measuring function according to claim 3 comprises:

a wearable casing having a display mounted on its front;

electrodes appearing on the surface of the casing for measuring the bioelectrical impedance of a person who is using the device;

personal data inputting means for inputting the sex, age, height and weight of the person;

body fat percentage calculating means for determining the body fat percentage of the person from the personal data and the bioelectrical impedance of the person;

basal metabolism calculating means for calculating the amount of the basal metabolism of the person from the personal data and the body fat percentage of the person;

means for presetting a given body fat percentage as a goal;

"to-be-reduced" body fat amount calculating means for determining the amount of "to-be-reduced" body fat from the difference between the present body fat percentage and the given body fat percentage preset as the goal;

"to-be-reduced" calorie amount calculating means for calculating the calorie amount to be reduced for consuming the amount of "to-be-reduced" body fat;

"to-be-attained" exercise amount setting means for changing the amount of "to-be-reduced" body fat to the "to-be-attained" exercise amount by taking the amount of the basal metabolism of the person into account and for setting the "to-be-attained" exercise amount as a goal; and exercise amount measuring means responsive to two- or three-dimensional movement for determining which mode of movement and measuring the amount of exercise;

whereby the "to-be-attained" exercise amount and the actual exercise amount taken by the person in addition to the body fat percentage may be given in the display An exercise amount measuring device provided with a body fat measuring function according to claim 4 comprises:

a wearable casing having a display mounted on its front;

electrodes appearing on the surface of the casing for measuring the bioelectrical impedance of a person who is using the device;

personal data inputting means for inputting the sex, age, height and weight of the person;

body fat percentage calculating means for determining the body fat percentage of the person from the personal data and the bioelectrical impedance of the person;

basal metabolism calculating means for calculating the amount of the basal metabolism of the person from the personal data and the body fat percentage of the person;

means for presetting a given body fat percentage as a goal;.

"to-be-reduced" body fat amount calculating means for determining the amount of "to-be-reduced" body fat from the difference between the present body fat percentage and the given body fat percentage preset as the goal;

"to-be-reduced" calorie amount calculating means for calculating the calorie amount to be reduced for consuming the amount of "to-be-reduced" body fat;

"to-be-attained" exercise amount setting means for changing the amount of "to-be-reduced" body fat to the "to-be-attained" exercise amount by taking the amount of the basal metabolism of the person into account and for setting the "to-be-attained" exercise amount;

exercise amount measuring means responsive to two- or thee-dimensional movement for determining which mode of movement and measuring the amount of exercise.

consumed calorie amount measuring means for determining the calorie amount reduced actually by the exercise from the so determined mode of movement, the so measured amount of exercise and the so calculated amount of the basal metabolism of the person;

remaining calorie amount calculating means for calculating the remaining calorie amount to be reduced by subtracting the actually reduced calorie amount from the "to-be-reduced" calorie amount; and remaining "to-be-attained" exercise amount calculating means for calculating the remaining "to-be-attained" exercise amount from the remaining calorie amount by taking the amount of the basal metabolism of the person into account;

whereby the remaining "to-be-attained" exercise amount in addition to the body fat percentage may be given in the display.

In an exercise amount measuring device provided with a body fat measuring function according to claim 5 as described in claims 1, 2, 3, and 4, the amount of exercise is determined by the product of the strength of exercise and the length of time for which the person takes an exercise.

In an exercise amount measuring device provided with a body fat measuring function according to claim 6 as described in claims 1, 2, 3, and 4, the exercise amount measuring means comprises a motion counter for counting how many times the person moves his or her body in two or three dimensions, and an accelerator for determining at what acceleration the person moves his or her body in two or three dimensions.

BEST MODES OF REDUCING THE INVENTION TO PRACTICE

Preferred embodiments of the present invention will be described below with reference to accompanying drawings.

Figure 1:
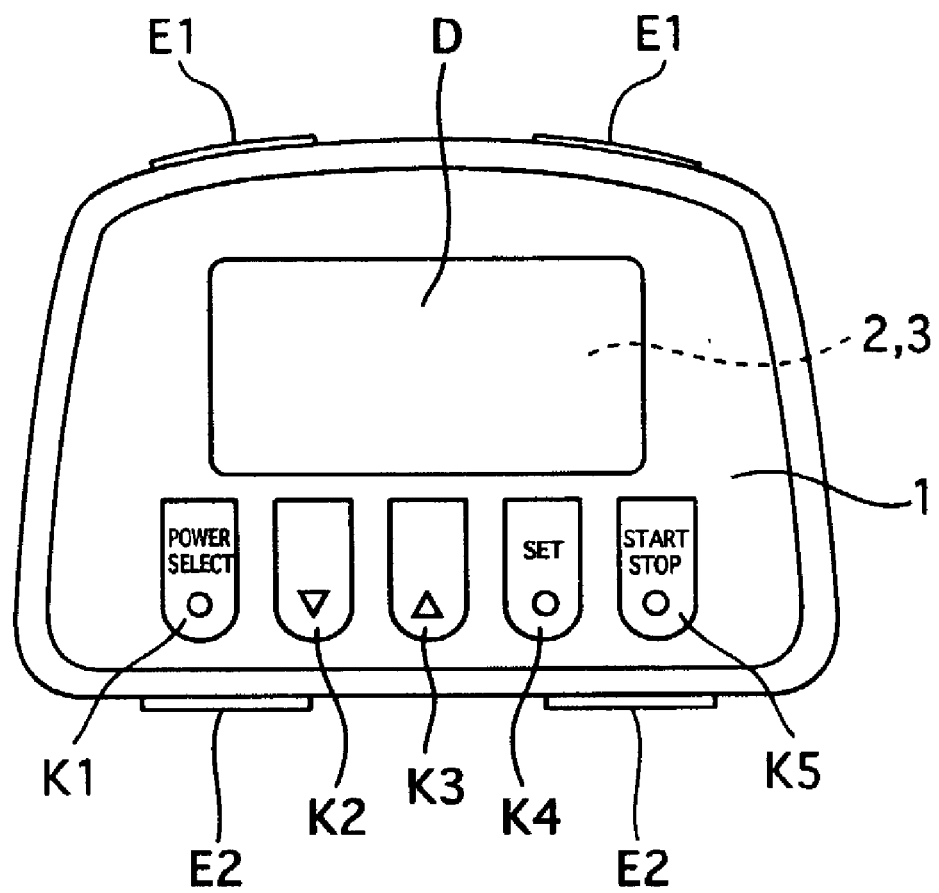
FIG. 1 is a front view of an exercise amount measuring device provided with a body fat measuring function according to one embodiment of the present invention.

FIG. 1 is a front view of an exercise amount measuring device provided with a body fat measuring function according to one embodiment of the present invention.

The exercise amount measuring device has a bioelectrical impedance measuring circuit 2, an accelerator 3 and a motion counter (not shown) installed in its casing 1. The casing 1 has a liquid crystal display D mounted on its front side, and two feeding electrodes E1 and E1 and two detecting electrodes E2 and E2 mounted on its upper and lower lateral sides. A power/selection key K1, a digit-descending key K2, a digit-rising key K3, a setting key K4 and a start/finish key K5 are arranged below the LCD on the front side of the casing 1.

A two second-long depression of the power/selection key K1 makes the power supply turn on, and another two second-long depression makes the power supply off. Each depression of the power/selection key K1 makes inputted data and displayed data appear alternately in the LCD.

Each and every depression of the digit-descending key K2 makes the number appearing in the LCD decrease one by one whereas each and every depression of the digit-rising key K3 makes the number appearing in the LCD increase one by one.

In inputting personal data such as the sex, age, height and weight their "default" values appear to be decreased or increased toward their correct values by depressing the digit-descending key K2 or the digit-rising key K3 as many times as required.

Every time each "default" value has reached the correct value, the setting key K4 is depressed to fix the correct value, and this is repeated until all correct values of personal data have been fixed.

Depression of the start/finish key K5 starts measurement of the body fat percentage and the amount of exercise. The display D shows all personal data, that is, the sex, age, height and weight of the user, body fat percentage, amount of the basal metabolism, body shape, amount of exercise, amount of calorie to be consumed, all measured or calculated, and amount of the body fat to be reduced for attaining a given body fat percentage set as a goal, amount of exercise and calorie required for losing the "to be reduced" amount of body fat and other pieces of information.

Figure 2:
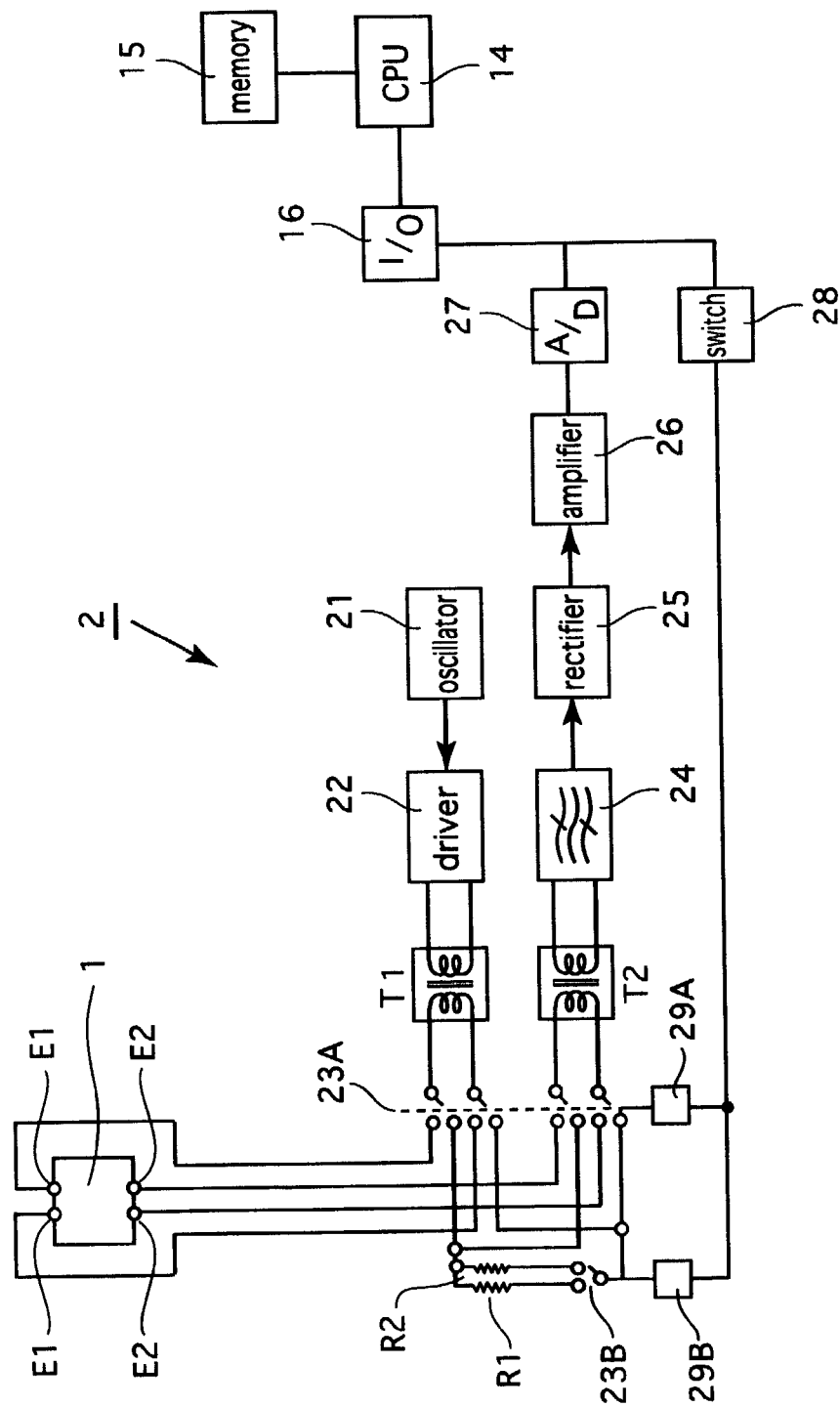
FIG. 2 is a wiring diagram of a bioelectrical impedance measuring circuit installed in the exercise amount measuring device equipped with the body fat gauge.

FIG. 2 shows a wiring diagram of a bioelectrical impedance measuring circuit installed in the exercise amount measuring device.

As shown in the drawing, the bioelectrical impedance measuring circuit 2 provides sinusoidal voltage of 50 kHz generated by a frequency generator 21 to the opposite feeding electrodes E1 and E1 of the casing 1 via a drive circuit 22; a transformer T1, and a switch 23A.

Figure 3:
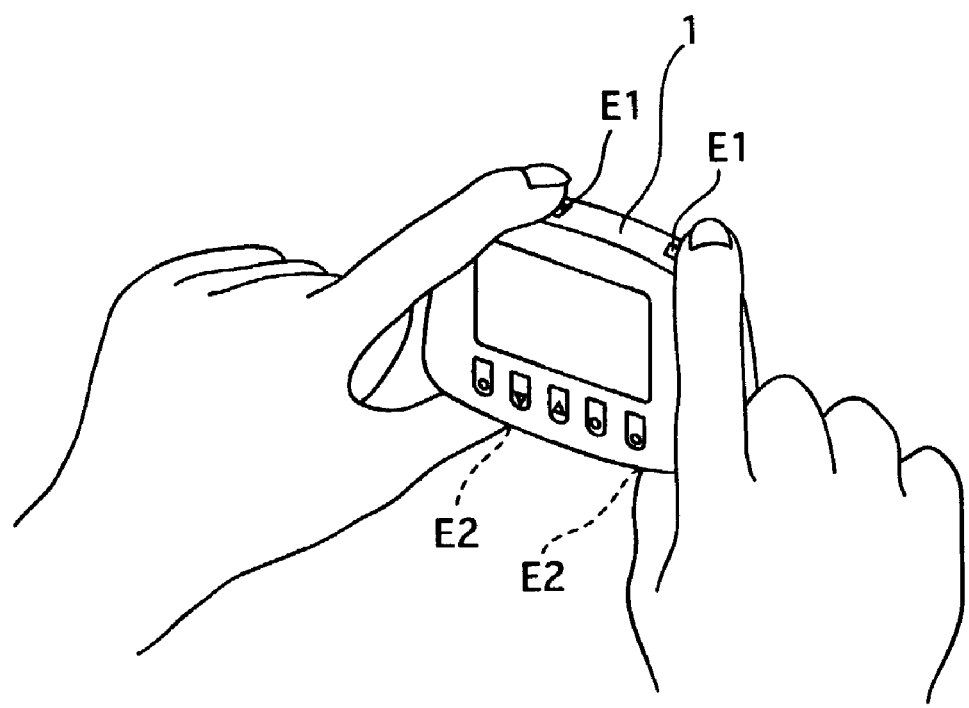
FIG. 3 illustrates how the exercise amount measuring device equipped with the body fat gauge is used.

When the bioelectrical impedance is measured, both arms extend straight forward at the level of the shoulder, and the fore-fingers and thumbs of both hands are applied to the feeding and detecting electrodes El and E2 of the casing 1 in pinching way, as shown in FIG. 3.

Thus, the voltage appearing between the opposite detecting electrodes E2 and E2 can be determined as the bioelectrical impedance appearing between the opposite hands.

Specifically the voltage appearing between the opposite detecting electrodes E2 and E2 is converted to a DC voltage via the contact arm 23A, the transformer T2, the band-pass filter 24, the rectification circuit 25 and the amplifier 26, and the reshaped, level-shifted and offset-adjusted voltage is directed to the analogue-to-digital converter 27, and to the CPU 14 via the I/O interface 16.

To reduce any error in measurement which would be caused if the characteristics of some parts should change with time and temperature, the bioelectrical impedance measuring circuit is calibrated in terms of its outputting characteristics on the detection side prior to measurement of the bioelectrical impedance.

Specifically, a regression linear equation representing the detected voltage-and-bioelectrical impedance relationship is given by $Z = k\, V + C_0$. The proportional constant k and the fixed constant $C_0$ can be determined by applying to known resistors R1 and R2 the same ac voltage as used in measuring the bioelectrical impedance Z and by measuring the voltages V appearing across the resistors R1 and R2.

Therefore, a control signal is sent from the CPU 14 via the I/O interface 16, the switch actuator 28, and the switching control circuit 29A so that the contact arm 23A may be thrown on the side on which the resistor R1 and R2 is connected between output side of T1 and input side of T2. Then, another control signal is sent from the CPU 14 via the I/O interface 16, the switch actuator 28, and the switching control circuit 29B so that the contact arm 23B may be thrown on the resistor R2 or R1.

Figure 4:
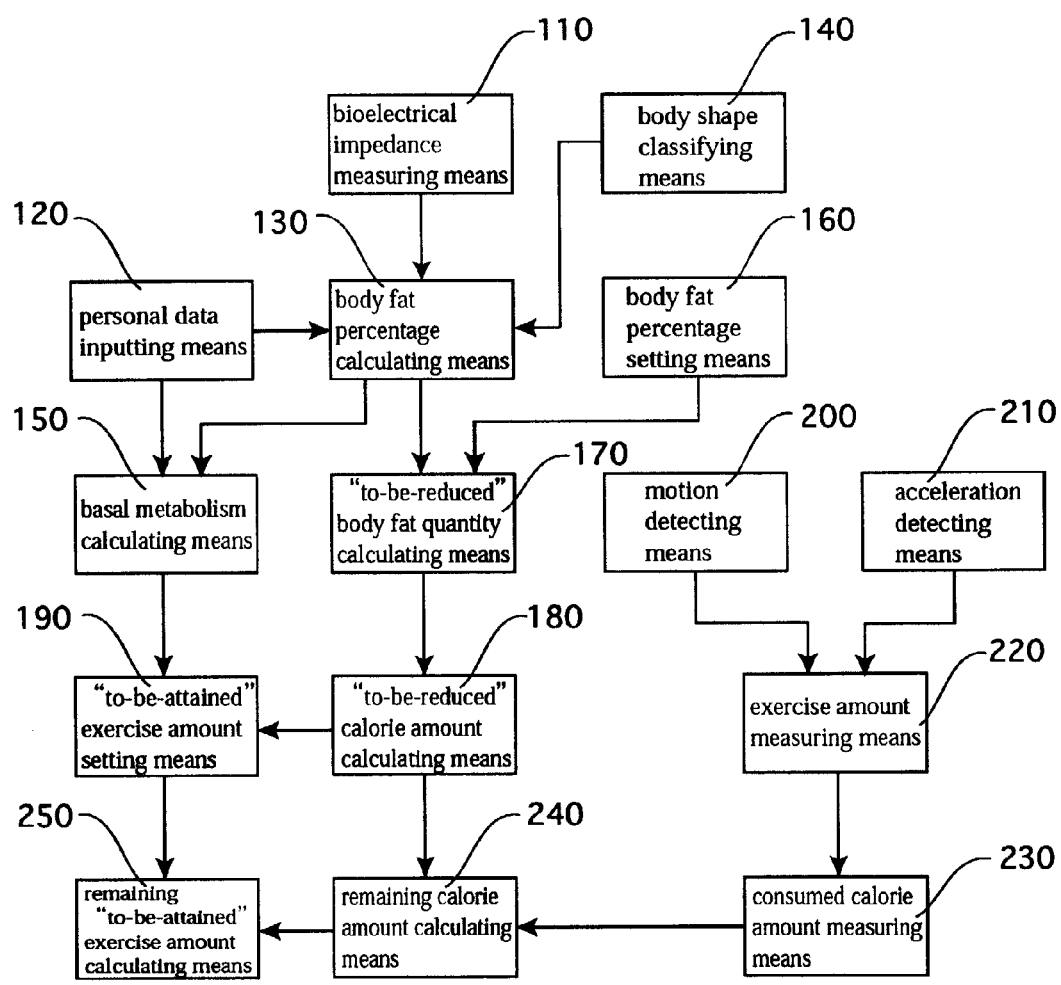
FIG. 4 illustrates what components make up the exercise amount measuring device equipped with the body fat gauge.

FIG. 4 is a block diagram of the exercise amount measuring device provided with a body fat measuring function.

As shown in the drawing, it comprises: a bioelectrical impedance measuring means 110 which is capable of measuring the bioelectrical impedance of a person holding the casing 1 of the device with his or her fingers applying to the electrodes of the casing; a personal data inputting means 120 for inputting the sex, age, height and weight of the person; a body fat percentage calculating means 130 for determining the body fat percentage of the person from the personal data and the bioelectrical impedance of the person; a body shape classifying means 140 for making a decision as to which type the body shape of the person belongs to on the basis of the personal data and the body fat percentage; a basal metabolism calculating means 150 for calculating the amount of the basal metabolism of the person from the personal data and the body fat percentage of the person; a body fat percentage setting means 160 for setting a given body fat percentage as a goal; a "to-be-reduced" body fat quantity calculating means 170 for determining the amount of the "to-be-reduced" body fat from the difference between the present body fat percentage and the given body fat percentage; a "to-be-reduced" calorie amount calculating means 180 for calculating the calorie amount to be reduced for consuming the amount of the "to-be-reduced" body fat; a "to-be-attained" exercise amount setting means 190 for calculating the "to-be-attained" exercise amount from the amount of the "to-be-reduced" body fat and for setting the so calculated "to-be-attained" exercise amount as a goal; a motion detecting means 200 for detecting two- or three-dimensional movement of the body; an acceleration detecting means 210 for detecting the acceleration of the two- or three-dimensional movement; an exercise amount measuring means 220 for measuring the amount of exercise actually taken on the basis of the detected movement and acceleration; a consumed calorie amount measuring means 230 for determining the calorie amount consumed actually by the exercise from the measured amount of exercise; a remaining calorie amount calculating means 240 for calculating the remaining calorie amount to be consumed by subtracting the actually consumed calorie amount from the "to-be-reduced" calorie amount; and a remaining "to-be-attained" exercise amount calculating means 250 for calculating the remaining "to-be-attained" exercise amount from the remaining calorie amount.

Figure 5:
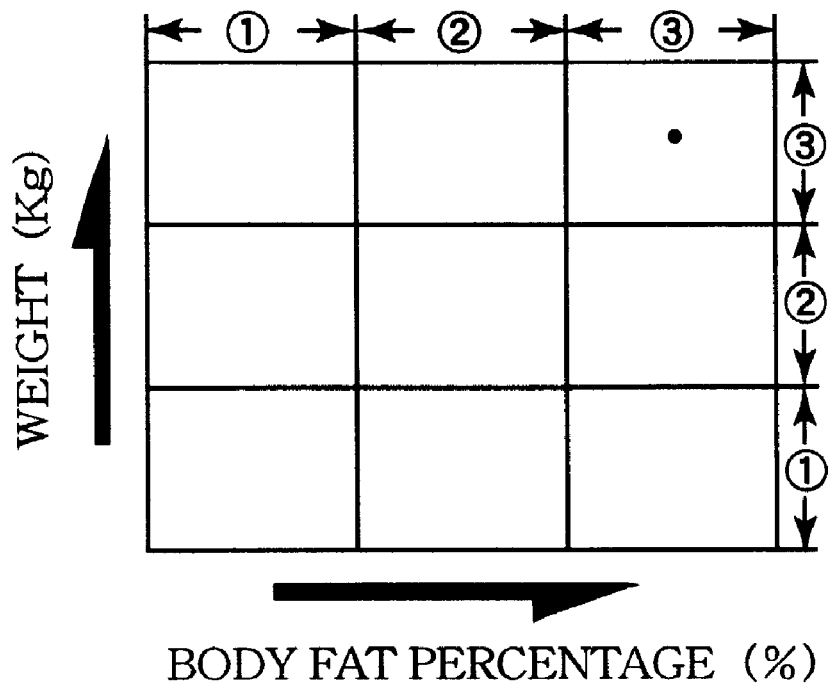
FIG. 5 illustrates how one's physical feature can be determined in terms of weight versus body fat percentage.

FIG. 5 shows a 3×3-sectioned lattice matrix with a vertical weight dimension and horizontal body fat percentage dimension. Each dimension includes three sections, that is, "below a normal health range"①, "a normal health range"② and "above a normal health range"③. The body shape classifying means 140 makes a decision on the body shape of the person in terms of which section of the matrix the weight of the person (inputted by the inputting means 120) and the body fat percentage (calculated by the body fat percentage calculating means 130) cross (see the dot in FIG. 5).

The "normal health range" of the weight covers the ideal weight times 0.9 to the ideal weight times 1.1. The ideal weight is given by: (height−100)×0.9×0.91. The "normal health range" of the body fat percentage covers 17 to 24 percent for women, and 14 to 20 percent for men. The nine sections of the matrix indicate "very athletic type", "athletic type", "overweight type", "ideal athletic type", "ideal healthy type", "extra overweight type", "extra slender type", "slender type" and "ultra overweight type" in the upper to lower weight-range order and in the left to right body fat percentage-range order.

The basal metabolism calculating means 150 calculates the amount of the basal metabolism of the person from the following equation:

the amount of the basal metabolism=$C_0$×weight× (100−body fat percentage)/100+$C_1$, where $C_0$ is equal to: 24.0349 for women at the age of 39 or less;

21.951 for women at the age of 40 or more;

27.717 for men at the age of 39 or less; and 25.333 for men at the age of 40 or more; and $C_1$ is equal to: 427.64 for women at the age of 39 or less;

424.38 for women at the age of 40 or more;

188.21 for men at the age of 39 or less; and 243.28 for men at the age of 40 or more The body fat percentage setting means 160 sets a given body fat percentage as a goal, which may be selected among healthy body fat percentages ranging from 17 to 24% for women and from 14 to 20% for men of the present body fat percentage.

The "to-be-reduced" body fat amount calculating means 170 determines the amount of the "to-be-reduced" body fat from the difference between the body fat percentage measured at present and the given body fat percentage set as the goal as follows:

the amount of the "to-be-reduced" body fat (Kg)=(the body fat percentage measured at present−the goal body fat percentage)/100×weight (Kg)

The amount of the "to-be-reduced" body fat is zero if the body fat percentage measured at present is smaller than the goal body fat percentage.

The "to-be-reduced" calorie amount calculating means 180 calculates the calorie amount to be reduced for consuming the amount of the "to-be-reduced" body fat by taking the following body fat-to-calorie relation into account: 7000 Kcal needs to be consumed to reduce the body fat of 1 Kg. Thus:

the calorie amount to be consumed (Kcal)=the amount of the "to-be-reduced" body fat (Kg)×7000 (Kcal/Kg)

The "to-be-attained" exercise amount setting means 190 sets the "to-be-attained" exercise amount as a goal by replacing the "to-be-reduced" calorie amount by the corresponding amount of exercise. The amount of exercise is given by the product of the strength of exercise and the length of time for which the person continues to take an exercise:

the amount of exercise (Kcal)=the strength of exercise (Kcal/minute)×the length of time for continuing the exercise (minutes)

The strength of exercise is given in terms of the calorie amount consumed per minute in taking an exercise:

the strength of exercise (Kcal/minute)=(metabolism-to-energy conversion rate×the amount of the basal metabolism+the amount of the metabolism at rest) (Kcal)/1440 (minutes)

The metabolism-to-energy conversion rate is dependent on the kind of exercise, representing how many times of the amount of the basal metabolism can be consumed by taking a selected exercise, as for instance follows: 2.0 for a slow walk; 3.0 for an ordinary walk; 5.0 for a quick walk and 7.0 for a run, all measured actually when taking the exercise. The amount of the metabolism at rest is equal to 1.2 times the amount of the basal metabolism.

The strengths of exercise for different kinds of exercise are as follows:

the strength of exercise for a slow walk (Kcal/minute)= (2.0×basal metabolism amount+metabolism amount at rest) (Kcal)/1440 (minutes);

the strength of exercise for an ordinary walk (Kcal/minute)=(3.0×basal metabolism amount+metabolism amount at rest) (Kcal)/1440 (minutes);

the strength of exercise for a quick walk (Kcal/minute)= (5.0×basal metabolism amount+metabolism amount at rest) (Kcal)/1440 (minutes); and the strength of exercise for a run (Kcal/minute)= (7.0×basal metabolism amount+metabolism amount at rest) (Kcal)/1440 (minutes);

Next, the length of time for which a selected exercise is being taken to consume the "to-be-reduced" calorie amount can be determined by:

exercise time (minutes)=the "to-be-reduced" calorie amount (Kcal)/the strength of exercise for the selected exercise (Kcal/minute).

Thus, the goal amount of exercise can be given for a different exercise, as for instance follows: 5000 minutes for an ordinary walk; 3000 minutes for a quick walk and such like.

Minimum time involved for starting the burning of body fat, that is, twelve or more minutes must be added to the exercise time.

The motion detecting means 200 comprises a two- or three-axial pendulum responsive to the movement of one's body for swinging, a magnet attached to the pendulum and a reed switch for turning on and off every time the magnet of the pendulum crosses the reed switch, thereby counting how often the body moves.

Figure 6:
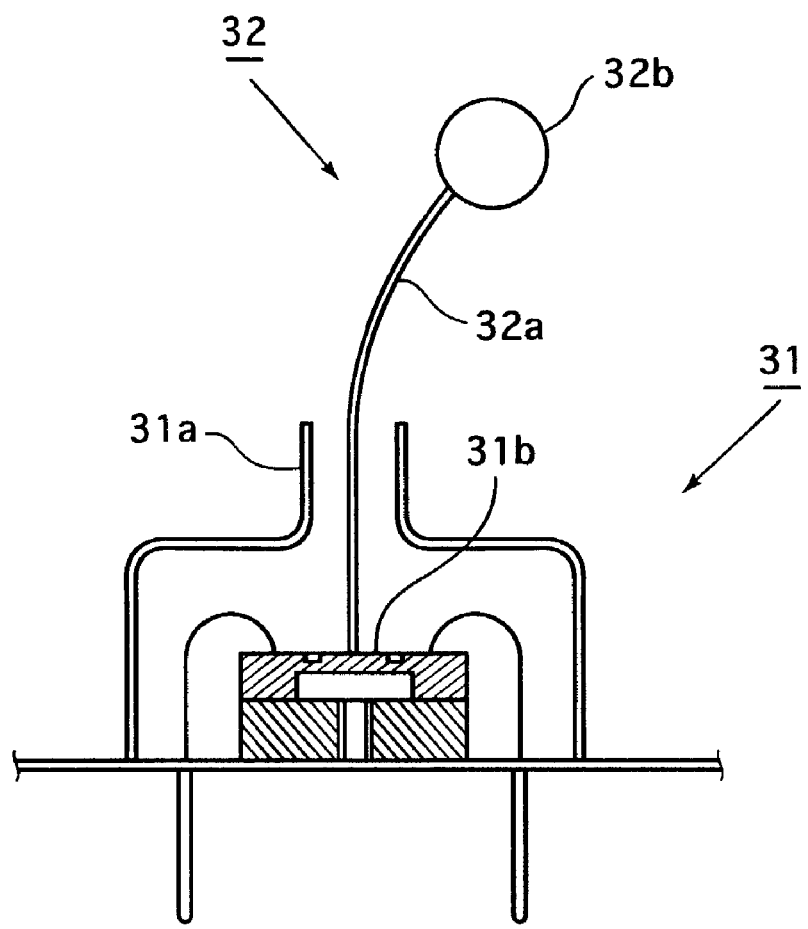
FIG. 6 shows, in section, an acceleration measuring device.

The acceleration detecting means 210 comprises an acceleration meter for detecting the acceleration of the two- or three-dimensional movement of the body. Referring to FIG. 6, it comprises a semiconductor pressure sensor 31 having a pendulum 32 swingably projecting from its port 31*a*. The pendulum 32 is a flexible spring wire 32*a* having a weight 32*b* fixed to its top, and the flexible spring wire 32*a* is fixed to a silicon diaphragm 31*b*, which provides a strain gauge.

The weight-headed spring wire 32*b* swings in all directions when the body moves, and accordingly the silicon diaphragm 31*b* is deformed to cause piezoelectric resistance effect representative its deformation, resulting in appearance of a bridge voltage representing the acceleration. The bridge voltage is amplified by an associated high-gain amplifier. Thus, the acceleration can be measured.

Another examples of acceleration meter 3 may use a strain gauge responsive to movement of a spring-suspended weight for determining the acceleration in terms of displacement of the weight; a piezoelectric element so loaded with a weight as to respond to displacement of the weight for changing the amount of static electricity appearing across the piezoelectric element, thus determining the acceleration in terms of the static electricity; or an electric coil-and-weight suspended in the magnetic field to induce an electromotive force when the electric coil-and-weight crosses the magnetic field in response to movement of the living body, thereby measuring the acceleration in terms of the induced electromotive force.

The exercise amount measuring means 220 is responsive both to the count provided by the motion detector and to the voltage appearing at the output terminal of the acceleration meter 3 for determining the length of time for which the person takes which mode of movement, selected among a slow walk, ordinary walk, quick walk and run.

The living body moves largely at an increased pitch as it moves quickly. Thus, the acceleration meter 3 can distinguish and identify which mode of movement.

In a case that the motion detector remains inoperative in spite of the operation of the acceleration meter 3, the person is not moving for instance, when riding on a vehicle, and in such a case the exercise measuring device is put in such a position that a wrong decision that the person takes an exercise cannot be made.

The consumed calorie amount measuring means 230 determines the strength of exercise on the basis of the mode of movement identified by the motion detecting means 220 to determine the calorie amount consumed actually by the exercise by multiplying the strength of exercise by the length of time for which the person has taken the exercise:

the calorie amount consumed actually by the exercise (Kcal)=Σ{the strength of exercise (Kcal/minute) for each mode of movement×exercise time (minutes)}

The remaining calorie amount calculating means 240 calculates the remaining calorie amount to be consumed by subtracting the actually consumed calorie amount (determined by the consumed calorie quantity measuring means 230) from the "to-be-reduced" calorie amount (determined by the "to-be-reduced" calorie amount calculating means 180):

the remaining calorie amount to be consumed (Kcal)=the "to-be-reduced" calorie amount (Kcal)−the actually consumed calorie amount (Kcal)

Every time the body fat percentage is measured anew, the "to-be-reduced" calorie amount is set again, and the remaining calorie amount to be consumed is equal to the "to-be-reduced" calorie amount thus set.

The remaining "to-be-attained" exercise amount calculating means 250 determines the remaining "to be consumed" calorie amount (determined by the remaining calorie amount calculating means 240) in terms of the remaining "to-be-attained" exercise amount, which is given for each different mode of movement:

the remaining length of exercise time for each mode of movement (minutes)=the remaining "to be consumed" calorie amount (Kcal)/the strength of movement for each mode of movement (Kcal/minute)

The exercise amount measuring device according to the present invention is constructed as described above, and the manner of using the same is described below.

In measuring the body fat percentage, first, the power/selection key K1, the digit-descending key K2, the digit-rising key K3 and the fixing key 4 are used to input the sex, age, height and weight of the user. The inputting operation is unnecessary if such personal data remains as they were last time.

Next, the start/finish key K5 is depressed, and then, the casing 1 is held by pinching the electrodes appearing on the upper and lower lateral sides of the casing with the forefingers and thumbs of both hands, thus starting the measurement of the body fat percentage.

After a while the body fat percentage appears in the display D, and at the same time, a single dot appears in a selected square of the matrix lattice, showing which type of body shape the person's body belongs to.

Depression of the power/selection key K1 makes the amount of the basal metabolism appear in the display D. In a case that the measured body fat percentage is above the healthy body fat percentage, each and every depression of the power/selection key K1 makes displayed information change, allowing the "to-be-reduced" body fat percentage (%), the "to-be-reduced" body fat amount (Kg), the amount of exercise and other values set as goals one after another.

The said values set as goals are recalculated each time a body fat is measured.

Depression of the start/finish key K5 makes the measurement of the amount of exercise start.

Thereafter, each and every depression of the power/selection key K1 makes the displayed information change, allowing the remaining "to-be-attained" amount of exercise, the actual amount of exercise, the remaining "to-be-reduced" calorie amount, the actually consumed calorie amount to appear in the display one after another.

INDUSTRIAL APPLICABILITY

As may be apparent from the above, an exercise amount measuring device provided with a body fat measuring function according to the present invention is responsive to a two- or three dimensional movement of the living body for calculating the calorie amount consumed by an exercise on the basis both of the amount of exercise measured, mode of movement determined and of the amount of the basal metabolism.

Calculation made by taking the mode of movement and the amount of the basal metabolism of the individual into account improves the accuracy with which the calorie amount consumed by an exercise is determined significantly over the accuracy of calculation irrespective of the amount of the basal metabolism.

Assuming that a person using the device changes slow walk to ordinaiy walk or quick walk to run, the device is responsive to the change in the mode of movement for providing a correct amount of exercise.

The exercise amount measuring device according to the present invention permits a given body fat percentage to be set as a goal, showing on the display both the "to-be-reduced" calorie amount for reaching the goal and the remaining "to-be-consumed" calorie amount, which is determined by subtracting the calorie amount actually consumed from the "to-be-reduced" calorie amount.

Thus, a person using the device can realize how far the person has been on the way to the goal, thereby not allowing him to lose his interest in continuing the exercise. As a result he can be increasingly eager to continue to take the exercise with the most concentrated attention, causing a surprising effect in a short time.

The exercise amount measuring device according to the present invention permits a given body fat percentage to be set as a goal, showing on the display both the "to-be-consumed" amount of exercise required for reaching the goal and the remaining "to-be-attained" amount of exercise calculated by subtracting the actual amount of exercise from the "to-be-consumed" amount of exercise.

Thus, a person using the device can realize how long and what strength of exercise the person has to continue at a glance to the display, thereby permitting him to control the amount of exercise appropriately for the purpose.

The exercise amount measuring device according to the present invention can measure the amount of exercise by using a motion gauge capable of counting a two- or three-dimensional movement of the living body and an acceleration meter capable of measuring the acceleration of the two- or three-dimensional movement of the living body.

Thus, different from the pedometer responsive only to the vertical motion of the living body, all moves in all directions can be detected, and therefore, the total amount of exercise including daily motions can be determined.

Combination of the motion gauge and the accelerator is effective to be insensitive to acceleration-free movement, so that the device may be guaranteed to be free of erroneous estimation of the amount of exercise, which otherwise, would be caused for instance, when the person is riding a vehicle.

What is claimed is:

1. An exercise amount measuring device provided with a body fat measuring function comprising:
   a wearable casing having a display mounted on its front;
   electrodes appearing on the surface of the casing for measuring the bioelectrical impedance of a person who is using the device;
   personal data inputting means for inputting the sex, age, height and weight of the person;
   body fat percentage calculating means for determining the body fat percentage of the person from the personal data and the bioelectrical impedance of the person;
   basal metabolism calculating means for calculating the amount of the basal metabolism of the person from the personal data and the body fat percentage of the person;
   means for presetting a given body fat percentage as a goal;
   "to-be-reduced" body fat amount calculating means for determining the amount of "to-be-reduced" body fat from the difference between the present body fat percentage and the given body fat percentage preset as the goal;
   "to-be-reduced" calorie amount calculating means for calculating the calorie amount to be reduced for consuming the amount of "to-be-reduced" body fat;
   exercise amount measuring means responsive to two- or three-dimensional movement for determining which mode of movement and for measuring the amount of exercise; and
   consumed calorie amount measuring means for determining the calorie amount consumed actually by the exercise from the so determined mode of movement, the so measured amount of exercise and the so calculated amount of the basal metabolism of the person; whereby the "to-be-reduced" calorie amount and the calorie amount actually consumed by the exercise taken by the person in addition to the body fat percentage may be given in the display.

2. An exercise amount measuring device provided with a body fat measuring function according to claim 1, wherein the amount of exercise is determined by the product of the strength of exercise and the length of time for which the person takes an exercise.

3. An exercise amount measuring device provided with a body fat measuring function according to claim 1, wherein the exercise amount measuring means comprises a motion counter for counting how many times the person moves his or her body in two or three dimensions, and an acceleration meter for determining at what acceleration the person moves his or her body in two or three dimensions.

4. An exercise amount measuring device provided with a body fat measuring function comprising:
   a wearable casing having a display mounted on its front;
   electrodes appearing on the surface of the casing for measuring the bioelectrical impedance of a person who is using the device;
   personal data inputting means for inputting the sex, age, height and weight of the person;
   body fat percentage calculating means for determining the body fat percentage of the person from the personal data and the bioelectrical impedance of the person;
   basal metabolism calculating means for calculating the amount of the basal metabolism of the person from the personal data and the body fat percentage of the person;
   means for presetting a given body fat percentage as a goal;
   "to-be-reduced" body fat amount calculating means for determining the amount of "to-be-reduced" body fat from the difference between the present body fat percentage and the given body fat percentage preset as the goal;
   "to-be-reduced" calorie amount calculating means for calculating the calorie amount to be reduced for consuming the amount of "to-be-reduced" body fat;
   exercise amount measuring means responsive to two- or three-dimensional movement for determining which mode of movement and for measuring the amount of exercise;
   consumed calorie amount measuring means for determining the calorie amount reduced actually by the exercise from the so determined mode of movement the so measured amount of exercise and the so calculated amount of the basal metabolism of the person; and
   remaining calorie amount calculating means for calculating the remaining calorie amount to be reduced by subtracting the actually consumed calorie amount from the "to-be-reduced" calorie amount; whereby the remaining calorie amount in addition to the body fat percentage may be given in the display.

5. An exercise amount measuring device provided with a body fat measuring function according to claim 4, wherein the amount of exercise is determined by the product of the strength of exercise and the length of time for which the person takes an exercise.

6. An exercise amount measuring device provided with a body fat measuring function according to claim 4, wherein the exercise amount measuring means comprises a motion counter for counting how many times the person moves his or her body in two or three dimensions, and an acceleration meter for determining at what acceleration the person moves his or her body in two or three dimensions.

7. An exercise amount measuring device provided with a body fat measuring function comprising:
   a wearable casing having a display mounted on its front;
   electrodes appearing on the surface of the casing for measuring the bioelectrical impedance of a person who is using the device;

personal data inputting means for inputting the sex, age, height and weight of the person;

body fat percentage calculating means for determining the body fat percentage of the person from the personal data and the bioelectrical impedance of the person;

basal metabolism calculating means for calculating the amount of the basal metabolism of the person from the personal data and the body fat percentage of the person;

means for presetting a given body fat percentage as a goal;

"to-be-reduced" body fat amount calculating means for determining the amount of "to-be-reduced" body fat from the difference between the present body fat percentage and the given body fat percentage preset as the goal;

"to-be-reduced" calorie amount calculating means for calculating the calorie amount to be reduced for consuming the amount of "to-be-reduced" body fat;

"to-be-attained" exercise amount setting means for calculating the "to-be-attained" exercise amount from the amount of "to-be-reduced" body fat by taking the amount of the basal metabolism of the person into account and for setting the so calculated "to-be-attained" exercise amount as a goal; and, exercise amount measuring means responsive to two- or three-dimensional movement for determining which mode of movement and for measuring the amount of exercise; whereby the "to-be-attained" exercise amount and the actual amount of exercise taken by the person in addition to the body fat percentage may be given in the display.

8. An exercise amount measuring device provided with a body fat measuring function according to claim 7, wherein the amount of exercise is determined by the product of the strength of exercise and the length of time for which the person takes an exercise.

9. An exercise amount measuring device provided with a body fat measuring function according to claim 7, wherein the exercise amount measuring means comprises a motion counter for counting how many times the person moves his or her body in two or three dimensions, and an acceleration meter for determining at what acceleration the person moves his or her body in two or three dimensions.

10. An exercise amount measuring device provided with a body fat measuring function comprising:

a wearable casing having a display mounted on its front;

electrodes appearing on the surface of the casing for measuring the bioelectrical impedance of a person who is using the device;

personal data inputting means for inputting the sex, age, height and weight of the person;

body fat percentage calculating means for determining the body fat percentage of the person from the personal data and the bioelectrical impedance of the person;

basal metabolism calculating means for calculating the amount of the basal metabolism of the person from the personal data and the body fat percentage of the person;

means for presetting a given body fat percentage as a goal;

"to-be-reduced" body fat amount calculating means for determining the amount of "to-be-reduced" body at from the difference between the present body fat percentage and the given body fat percentage preset as the goal;

"to-be-reduced" calorie amount calculating means for calculating the calorie amount to be reduced for consuming the amount of "to-be-reduced" body fat, "to-be-attained" exercise amount setting means for calculating the "to-be-attained" exercise amount from the amount of "to-be-reduced" body fat by taking the amount of the basal metabolism of the person into account and for setting the so calculated "to-be-attained" exercise amount as a goal;

exercise amount measuring means responsive to two- or three-dimensional movement for determining which mode of movement and for measuring the amount of exercise;

consumed calorie amount measuring means for determining the calorie amount reduced actually by the exercise from the so determined mode of movement, the so measured amount of exercise and the so calculated amount of the basal metabolism of the person;

remaining calorie amount calculating means for calculating the remaining calorie amount to be reduced by subtracting the actually reduced calorie amount from the "to-be-reduced" calorie amount; and remaining "to-be-attained" exercise amount calculating means for calculating the remaining "to-be-attained" exercise amount from the remaining calorie amount by taking the amount of the basal metabolism of the person into account; whereby the remaining "to-be-attained" exercise amount in addition to the body fat percentage may be given in the display.

11. An exercise amount measuring device provided with a body fat measuring function according to claim 10, wherein the amount of exercise is determined by the product of the strength of exercise and the length of time for which the person takes an exercise.

12. An exercise amount measuring device provided with a body fat measuring function according to claim 10, wherein the exercise amount measuring means comprises a motion counter for counting how many times the person moves his or her body in two or three dimensions, and an acceleration meter for determining at what acceleration the person moves his or her body in two or three dimensions.

* * * * *